United States Patent [19]
Douglas et al.

[11] Patent Number: 5,948,695
[45] Date of Patent: Sep. 7, 1999

[54] DEVICE FOR DETERMINATION OF AN ANALYTE IN A BODY FLUID

[75] Inventors: Joel S. Douglas, Santa Clara; Ryszard Radwanski, Morgan Hill; Brent G. Duchon, San Jose, all of Calif.; John H. Priest, Everett, Wash.; David A. Hasker, San Jose, Calif.; John M. Gleisner, Lynnwood, Wash.

[73] Assignee: Mercury Diagnostics, Inc., Scotts Valley, Calif.

[21] Appl. No.: 08/874,468

[22] Filed: Jun. 17, 1997

[51] Int. Cl.⁶ .................................................. G01N 33/543
[52] U.S. Cl. .............................. 436/518; 422/55; 422/56; 422/58; 435/287.1; 435/287.2; 435/287.7; 435/287.8; 435/287.9; 435/805; 435/810; 435/970; 436/164; 436/169; 436/170; 436/530; 436/805; 436/810
[58] Field of Search ..................... 422/55–58; 435/287.1, 435/287.2, 287.7, 287.8, 287.9, 805, 810, 970; 436/164, 169, 170, 518, 530, 805, 810

[56] References Cited

U.S. PATENT DOCUMENTS

| | | |
|---|---|---|
| 3,298,789 | 1/1967 | Mast . |
| 3,992,158 | 11/1976 | Przybylowicz et al. . |
| 4,042,335 | 8/1977 | Clement . |
| 4,144,306 | 3/1979 | Figueras . |
| 4,258,001 | 3/1981 | Pierce et al. . |
| 4,627,445 | 12/1986 | Garcia et al. . |
| 4,637,403 | 1/1987 | Garcia et al. . |
| 4,637,978 | 1/1987 | Dappen . |
| 4,734,360 | 3/1988 | Phillips . |
| 4,787,398 | 11/1988 | Garcia et al. . |
| 4,790,979 | 12/1988 | Terminiello et al. . |
| 4,818,677 | 4/1989 | Hay-Kaufman et al. ................... 435/4 |
| 4,824,639 | 4/1989 | Hildenbrand et al. . |
| 4,839,296 | 6/1989 | Kennedy et al. ........................ 436/170 |

(List continued on next page.)

FOREIGN PATENT DOCUMENTS

| | | |
|---|---|---|
| 0110173 | 6/1984 | European Pat. Off. . |
| 0140337 | 5/1985 | European Pat. Off. . |
| 0351891 | 1/1990 | European Pat. Off. . |
| 0453283 | 10/1991 | European Pat. Off. . |
| 0638805 | 2/1995 | European Pat. Off. . |
| 0656423 | 6/1995 | European Pat. Off. . |
| 0735369 | 10/1996 | European Pat. Off. . |
| 0759555 | 2/1997 | European Pat. Off. . |
| 0769558 | 4/1997 | European Pat. Off. . |
| 0799896 | 10/1997 | European Pat. Off. . |
| 20905659 | 7/1982 | United Kingdom . |
| WO 8501747 | 4/1985 | WIPO . |
| WO 9613707 | 5/1996 | WIPO . |

*Primary Examiner*—Christopher L. Chin
*Attorney, Agent, or Firm*—Burns, Doane, Swecker & Mathis, L.L.P.

[57] ABSTRACT

A strip for testing for the presence of an analyte generally comprises a support member which contains a spreading layer and a reagent layer, and a capillary tube in communication with the support layer and spreading layer for transporting a sample of body fluid thereto. A method of testing a fluid for the presence or concentration of an analyte is also provided which generally includes providing a test strip with a support member, a spreading layer, and a reagent layer on the spreading layer. A capillary tube is provided on the support member whereby a fluid containing an analyte to be tested is introduced into the tube and flows through the tube to the spreading layer and contacts the reagent layer.

12 Claims, 4 Drawing Sheets

U.S. PATENT DOCUMENTS

| | | |
|---|---|---|
| 4,900,666 | 2/1990 | Phillips . |
| 4,935,346 | 6/1990 | Phillips et al. . |
| 5,049,487 | 9/1991 | Phillips et al. . |
| 5,100,620 | 3/1992 | Brenneman ................................ 422/58 |
| 5,147,606 | 9/1992 | Charlton et al. . |
| 5,179,005 | 1/1993 | Phillips et al. . |
| 5,187,100 | 2/1993 | Matzinger et al. . |
| 5,211,914 | 5/1993 | Vogel et al. . |
| 5,279,294 | 1/1994 | Anderson et al. . |
| 5,304,468 | 4/1994 | Phillips et al. . |
| 5,306,623 | 4/1994 | Kiser et al. . |
| 5,366,902 | 11/1994 | Cox et al. ................................. 422/56 |
| 5,402,798 | 4/1995 | Swierczek et al. . |
| 5,418,142 | 5/1995 | Kiser et al. . |
| 5,426,032 | 6/1995 | Phillips et al. . |
| 5,445,967 | 8/1995 | Deuter . |
| 5,451,350 | 9/1995 | Macho et al. . |
| 5,507,288 | 4/1996 | Bocker et al. . |
| 5,515,170 | 5/1996 | Matzinger et al. . |
| 5,518,006 | 5/1996 | Mawhirt et al. . |
| 5,522,255 | 6/1996 | Neel et al. . |
| 5,526,120 | 6/1996 | Jina et al. . |
| 5,547,702 | 8/1996 | Gleisner . |
| 5,556,761 | 9/1996 | Phillips . |
| 5,563,031 | 10/1996 | Yu . |
| 5,580,794 | 12/1996 | Allen . |
| 5,620,863 | 4/1997 | Tomasco et al. . |

FIG_1

FIG_2

FIG_3

FIG_4

FIG_5

FIG_6

FIG_7

FIG_8

FIG_9

DEVICE FOR DETERMINATION OF AN ANALYTE IN A BODY FLUID

FIELD OF THE INVENTION

The present invention relates to a test device and determination of a chemical or biochemical component (analyte) in an aqueous body fluid, such as whole blood. In particular the present invention relates to a dry reagent test strip from which an analyte presence and/or concentration is determined by use of an instrument. A common use of such test strips is for determination of glucose level in blood by diabetics.

BACKGROUND OF THE INVENTION

Numerous devices have been developed to test for presence and quantity of analytes in aqueous samples, such as whole blood or urine. The patent and technical literature of the last thirty years is replete with inventions which utilize a reagent strip containing a dry chemistry reagent system, that is, a system in which the wet chemistries are imbibed into an absorbent or bibulous medium, dried, and later reconstituted by fluid from the test sample. The reagent strips contain an indicator which changes color, depending on the presence or concentration of a particular analyte in a biological fluid applied to the strip. These strips may be read visually by reference to a color standard or calorimetrically by instrument calibrated or programmed to detect a certain color. Although some of these strips use reduction chemistries, more commonly they involve an oxidizable dye or dye couple. Some of the strips include an enzyme, such as glucose oxidase, which is capable of oxidizing glucose to gluconic acid and hydrogen peroxide. They also contain an oxidizable dye and a substance having peroxidative activity, which is capable of selectively catalyzing oxidation of the oxidizable dye in the presence of hydrogen peroxide. (See, for example, U.S. Pat. No. 4,935,346, to Phillips et al.) Examples of these devices, in addition to those used to test blood glucose, include tests for cholesterol, triglycerides, calcium or albumin in whole blood, and for protein, ketones, albumin or glucose in urine.

Dry chemistry reagent strips incorporating enzyme-based compositions are used daily by millions of diabetics to determine blood glucose concentrations. The NIH sponsored study, the Diabetes Complications and Control Trial, demonstrated conclusively that careful control of blood glucose levels can significantly reduce the incidence of serious complications of diabetes such as vision loss and kidney malfunction. Most diabetics must test themselves periodically in order to make appropriate adjustments to their diet or medication. It is thus especially important for diabetics to have rapid, inexpensive, and accurate reagent strips for glucose determination. The embodiment of dry chemistry reagent systems in test strips enable simple yet effective analytical protocols.

The technologies embodied in the products which have been developed to date have certain limitations from the perspective of the end user and/or the manufacturer. Colorimetric strips that dose on the meter can lead to contamination of the meter. Further, many patients with arthritis or vision impairment have difficulty bring a drop of blood which is hanging on one of their fingers to a small application spot on the strip in the meter. Dosing off the meter, placing the sample on the strip and then inserting it into the meter, also can still lead to contamination. Electrochemical strips deal with the contamination issues, but the manufacturing difficulties and cost can be prohibitive.

There is, therefore, a need to overcome some of the limitations of currently available testing systems. U.S. Pat. No. 3,092,465, issued to Adams et al., U.S. Pat. No. 3,298,789, issued to Mast and U.S. Pat. No. 3,630,957, issued to Rey et al., all describe a basic reagent system which became a standard for colorimetric determination of glucose in biological samples. These patents describe the formation of a film layer or semi-permeable coating over the bibulous matrix to hold back the larger particulates, such as red blood cells, and allow fluid to permeate into the bibulous matrix. This approach requires the removal of red blood cells by washing or wiping to enable visual inspection or instrument reading of the indication of the dye color formed in the matrix.

Stone, U.S. Pat. No. 3,607,093, discloses a membrane for testing blood where the membrane has a skin permeable to solutions but impermeable to solids such as red blood cells and to macromolecules such as proteins. This membrane is disclosed as being used by applying a blood sample then wiping away the red blood cells from the skin in order to reach the test indication through the skin.

U.S. Pat. No. 3,552,928, issued to Fetter discloses the use of certain water soluble salts and amino acids in reagent formulations as separation agents to provide blood separation. With solids such as red blood cells substantially removed from the biological fluid, there is less background color at the test site to obscure a change in coloration produced by a testing reagent.

Phillips et al., U.S. Pat. No. 4,935,346 discloses a system wherein a whole blood sample is applied to the device and indicator development occurs in the presence of the colored components of the sample. Measurements of the color change in indicator are made at two distinct wavelengths to eliminate the interferences from the presence of colored blood components.

Terminello et al., U.S. Pat. No. 4,774,192, disclose a system in which the matrix is formed of an asymmetric material used to filter the red blood cells in the sample. The asymmetric material has a density gradient from one side to the other to progressively separate red blood cells from the fluids.

Daffern et al., U.S. Pat. No. 4,994,238, disclose a test device that comprises an asymmetric reagent layer that has progressively finer filtration with increased distance from one surface toward the other surface.

Castino et al., U.S. Pat. No. 5,456,835 disclose the use of filters formed of ligand modified polymeric film such as polypropylene fibers and polyethersulfone fibers.

Vogel et. al., U.S. Pat. No. 4,477,575, disclose the use of glass fiber material to achieve blood separation through the thickness of the material. Blood is applied to one side of the glass fiber, and relatively clear fluid migrates out of the opposite side. This fluid is delivered to an additional layer where the detection of analytes can occur.

Macho et al., U.S. Pat. No. 5,451,350, disclose the use of absorbent channels to distribute sample fluid in multi-zone test devices. Charlton et al., U.S. Pat. No. 5,208,163, also disclose the use of capillary channels to distribute blood to various chambers in the device.

The disclosures of the above patents are incorporated herein by reference.

The prior art devices and methods of the above references provide varying degrees of effectiveness of blood analysis at varying degrees of complexity and cost.

It is an object of the present invention to provide enhanced devices and methods to improve the performance and minimize the cost and complexity compared to the prior art devices.

It is another object of this invention to provide a capillary format for testing which is easy to sample and dose and to manufacture.

It is another object of this invention to provide a configuration or format for testing which permits the patient to use "non traditional" body locations, other than the fingertips to extract a sample of body fluids.

It is another object of this invention to provide a means for performing microtitration by limiting the volume of a bodily fluid used to perform the analysis.

It is another object of this invention to provide a means for delivering a measured volume of a bodily fluid to the test area.

It is still a further object of this invention to provide a dry chemistry reagent test strip which can be used in or read by an electronic meter to analyze body fluids for one or more analytes.

The above objects as well as others are achieved by the devices, methods and systems of this invention as disclosed herein.

SUMMARY OF THE INVENTION

In one aspect this invention provides a method of testing body fluids for the presence or concentration of an analyte by using a porous matrix. Pending U.S. patent application Ser. No. 08/628,489 filed Apr. 5, 1996 describes the use of microporous matrix material and the concept of microtitration which are well suited for use in this invention, the disclosure of which application is incorporated herein by reference.

In another aspect this invention provides a device that contains body fluids during testing that eliminates the problems of meter contamination, and it's simple colorimetric design greatly reduces the difficulties of manufacturing and cost.

In a preferred embodiment of the invention the device consists of a capillary system which is used to collect the sample of body fluid and deposit it onto a reagent membrane for analysis. The use of a capillary tube to collect the sample permits the patient to collect a sample from a non finger tip location thereby increasing the number of possible sampling sites from which to extract a sample of body fluid. The apparatus comprises of a hydrophilic capillary tube in communication with a hydrophilic capillary wicking or spreading material which is in communication with an absorbent reagent membrane. The reagent membrane has been imbibed with indicator reagent system capable of indicating the presence or concentration of the analyte.

In another aspect, this invention uses the concept of microtitration to limit the volume of the sample thereby improving the accuracy of the test. The capillary wick and/or the membrane is bounded to the injection molded capillary and handle thereby creating a defined volume for the absorption of the sample. The user applies a blood sample to the capillary by placing the capillary tube in communication with the sample and allowing it to wick up the tube and wet out the membrane. The fluid passes through the capillary spreading layer/filter onto the membrane. The reading or measuring for the presence/concentration of the analyte being tested is accomplished by detecting the change in reflectance of the reagents which are imbibed into the membrane. The embodiments of the devices of the invention with the appropriate dry chemistry system in the matrix member can be used in test strips which may be read or measured in an electronic meter.

In another aspect, this invention provides a strip for testing for the presence or concentration of an analyte in a fluid comprising a support member; a spreading layer on the first side of the support member; a reagent layer on the spreading layer which comprises a reagent selected for the analyte of interest; and a capillary tube on the opposite side of the support member communicating through an aperture in the support member with the spreading layer, whereby a fluid containing an analyte introduced into the tube flows through the tube and the spreading layer to contact the reagent. Optionally the strip can further comprise a carrier layer on the reagent layer and positioned on the other side of the reagent layer from the spreading layer and an aperture in the carrier layer for observing or measuring the indication of the reagent.

In another aspect, this invention provides a method of testing a fluid for the presence or concentration of an analyte comprising providing a test strip comprising a support member; a spreading layer on the first side of the support member; a reagent layer on the spreading layer which comprises a reagent selected for the analyte of interest; and a capillary tube on the opposite side of the support member communicating through an aperture in the support member with the spreading layer, whereby a fluid containing an analyte introduced into the tube flows through the tube and the spreading layer to contact the reagent; introducing sufficient fluid containing an analyte into the capillary tube to flow onto the reagent layer; and observing or measuring the indication of the reagent.

In another aspect, this invention provides a method of making a strip for testing for the presence or concentration of an analyte in a fluid comprising: providing a support member with a capillary tube positioned on one side of the support member and communicating with the opposite side of the support member through an aperture in the support member; mounting a spreading layer on the opposite side of the support member and in communication with the aperture in the support member; and mounting a reagent layer on the spreading layer. Optionally the method includes a method comprising: mounting a carrier strip on the reagent layer opposite the spreading layer; and providing an aperture in the carrier layer for observing or measuring the indication of the reagent. Preferably, the method includes preassembling the carrier layer, the reagent layer and the spreading layer; and mounting the preassembled layer on the support member.

The above sets forth the generic aspects of the device and methods of the present invention. These device and methods are more fully described in the drawings and the descriptions below.

DETAILED DESCRIPTION OF THE INVENTION

The devices of the present invention are simpler to use and are easier and less costly to manufacture than most devices previously available. The simplicity of use is especially important for diabetics who rely on blood glucose testing multiple times per day to keep their disease under control. For many diabetics, the costs associated with blood glucose monitoring are also important, especially elderly diabetics on fixed incomes. Devices of various configurations and various uses based on the embodiments of the invention disclosed herein can be delivered to the diabetic, in a more cost effective manner. The ease of use and ability to capture the blood sample provide a means to use non traditional sites on the body from which to extract a sample. This eliminates the need for the patient to continually use the finger tips as a sampling site. The convenience of these devices will facilitate increased patient compliance with recommended testing routines and will result in improved overall health of diabetic patients.

As used herein, reference is primarily made to blood. However, other fluids such as urine, saliva and the like can be analyzed utilizing the various embodiments of the present invention. One membrane used in the invention is preferably a polyethersulfone polymer, which is cast to inherently have a microporous skin on one side and a porous matrix on the other side, such as the Gelman membrane. However, one may also employ a matrix layer or membrane having uniform porosity but no barrier skin on either side by laminating to one side of such a matrix a microporous barrier film to form the required barrier skin on one side of the matrix.

The invention provides different mechanisms for using the dry chemistry reagent systems with or without microtitration volume control. The dry chemistry components and microtitration principles, which are described below and in the above referenced U.S. patent application Ser. No. 08/628,489, are well suited for this application, and are independent of the device embodiments which follow.

In this invention, the preferred method for controlling the test area geometry is to emboss or compress the capillary wick or spreading layer and membrane or reagent layer into the molded part, deforming a portion of the capillary wick and membrane into openings in the molded part and leaving the test area uncompressed. The molded part comprises the capillary tube, support member, optional handle, and preferably a recessed area molded to receive the capillary wick and the membrane. The compressed areas are fastened to the molded part with adhesive such as 3-M grade 415 acrylic pressure sensitive adhesive, creating a test area which is completely bounded on the sides, preventing any flow outside the area. The only means of sample entry to the membrane or reagent layer test area is via the capillary tube and capillary wick or spreading layer. The capillary wick and membrane are embossed into the molded part by bringing both pieces together and pressing them together which pushes a portion of the capillary wick and membrane into the gasket openings and deforms the material outside of the openings by compressing it so that the thickness is reduced by 80 to 95% in the compressed portion.

The fluid sample enters the microtitration zone in the capillary wick and membrane via the capillary tube in the molded part. As can be seen from the structure of the device of the present invention, the blood or body fluid sample is collected by the user by touching the extended end of the capillary tube to the blood or fluid available. This enables the user to create the blood sample at any desired location on the body, then collect it by contacting the capillary tube end therewith. This invention eliminates the need for the user to form a drop of blood or body fluid and drop it or place it on a strip or into an aperture or opening. Moreover, this invention eliminates the concern of the user over having appropriate volume of blood or test sample of fluid. When the user contacts the capillary tube of the device of the present invention to the blood or fluid drop, the present device fills itself with the appropriate volume then stops. So long as the user can see excess blood or fluid remaining and the capillary tube end fully wetted, the user can be confident sufficient sample has been taken up into the device. Although the capillary tube of the device of this invention may be touched to the body, contamination of other devices is eliminated due to the single use, disposable nature of the device, and contamination of the meter is eliminated due to the meter reading the side opposite from the capillary tube.

A wetting agent may be applied to the internal diameter of the capillary to facilitate blood flow. High molecular weight polymeric oils work well as wetting agents. A preferred material is dimethylsiloxane ethylene oxide, part number PS073 from United Chemical Technologies. The same effect may be achieved through the use of patterned hydrophilic printing inks, BSI Corporation Photolink™ hydrophilic surface treatment or by using a Cellulosic injection molded part. These materials work equally well. Selection of a polymer having hydrophilic surface properties may eliminate need for any wetting agents.

Separating agents can be impregnated into the reagent layer membrane and or the capillary wick spreading layer before, during or after the impregnation of test reagents. The specific compounds are selected to enhance the ability of the matrix to separate whole blood into red blood cells and relatively clear fluid. As discussed previously, the preferred matrix materials comprise a microporous polyethersulfone from Gelman, and spreading layers formed from Ahlstrom 1281 or Ahlstrom 1660, which are cellulose and glass media.

The separating agents which can be impregnated into the membrane and or capillary wick may be selected from the following: polyvinyl sulfonic acid (PVSA), polyethylene glycol (PEG), polystyrene sulfonic acid (PSSA), hydroxypropyl cellulose (commercially available as Klucel ™), polyvinyl alcohol (PVA), polyvinylpyrrolidone (PVP), polyacrylic acid (PAA), water soluble salts, citrates, formates and sulfates, amino acids, chitosan (amino sugar), citric acid, phytic acid and malic acid. These materials may be enhanced through combining with silica or clay. The chemical components can include equivalent materials which help to separate whole blood into red blood cells and relatively clear fluid.

The indicating reagent mix must be capable of detecting the presence of the analyte. In general, the analyte reacts with a specific oxidase enzyme and produces hydrogen peroxide. This strongly oxidative substance reacts with the indicator(s) present to produce a colored end product. The oxidase enzyme may be one of the following: glucose oxidase, cholesterol oxidase, uricase, alcohol oxidase, aldehyde oxidase or glycerophosphate oxidase. While the examples and preferred embodiments herein comprise glucose oxidase in the formulations, formulation changes required to utilize other oxidase enzymes are evident to one who is skilled in the art. The indicator chemistries which provide acceptable color generation when coated on the microporous membrane (polyethersulfone) may be chosen from 3-methyl-2-benzothiazolinone hydrazone hydrachloride (MBTH) combined with 3,3-dimethylaminobenzoic acid (DMAB), MBTH combined with 3,5-dichloro-2-hydroxybenzene-sulfonic acid (DCHBS); 4-aminoantipyrene (4-AAP) (at 4 mg/ml) and 5-Oxo-1-(p-sulfophenyl)-2-pyrazoline-3-carboxylic acid (OPSP); 4-AAP and n-(m-tolyl)-diethanolamine (NDA); 2,2'-azino-di (3-ethylbenzthiazoline) sulfonic acid (ABTS); 4AAP (at 4 mg/ml) and 4-methoxynaphthol; pyrogallol red(PGR); bromopyrogallol red (BPR), acid green 25 (AG); MBTH and 8-anilino-1-naphthalenesulfonate (ANS), or N-(3-sulfopropyl)aniline and MBTH; or other known and conventional dye system for different analytes. U.S. Pat. No. 5,306,623 to Kiser et. al. incorporated herein by reference discloses effective concentrations of a number of useful dye systems.

The above reagents will create a chemistry which can be read with a meter. The separation reagents, indicator reagents, oxidase enzymes, peroxidase enzymes, hematocrit adjuster, buffers, and chelators together with the dye system are impregnated in the membrane matrix forming the reagent layer.

The issue of hematocrit level affecting the accuracy of test results is a substantial one for a test device. The following embodiment of this invention can be used to compensate for the hematocrit variation of whole blood. The instrument can be designed with additional sensors. These sensors can either be electrical contacts or light sources and receivers (sensors) connected to analog signaling/conditioning circuit. These additional sensors can be implemented so that they inspect the capillary tubes in the test device, one sensor at the beginning of the capillary channel and one at the end. Whole blood is applied to the capillary. The entry flow of whole blood is timed as it moves between sensors. The time that the blood takes to travel the length of the tube capillary is an indication of the hematocrit of the blood. That information is used to correct any shift in reflectance readings of the instrument caused by the hematocrit level.

The various aspects of the invention disclosed herein can best be illustrated by reference to the drawings and the description thereof which follows.

Figure 1:
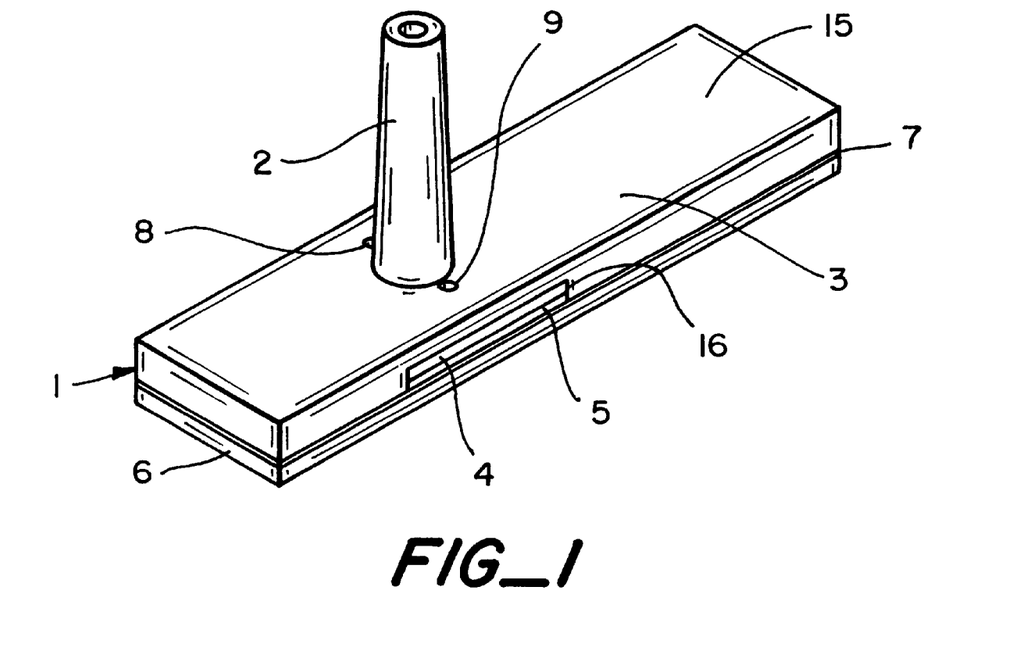
FIG. 1 is a perspective view of the capillary tube test strip assembly of this invention.

The capillary test strip 1 is shown in FIG. 1 and comprises of five components. The first part is the injection molded capillary tube 2 and support member 3 which comprises capillary tube 2, handle portion 15, vent holes 8 and 9, and slot or recess 16. The second component is the spreading/filtering layer 4 which is in communication with the membrane or reagent layer 5. The reagent layer membrane 5 is attached to a carrier layer 6 by adhesive layer 7. The adhesive layer 7 also attaches the carrier layer 6 to the support member 3.

Figure 2:
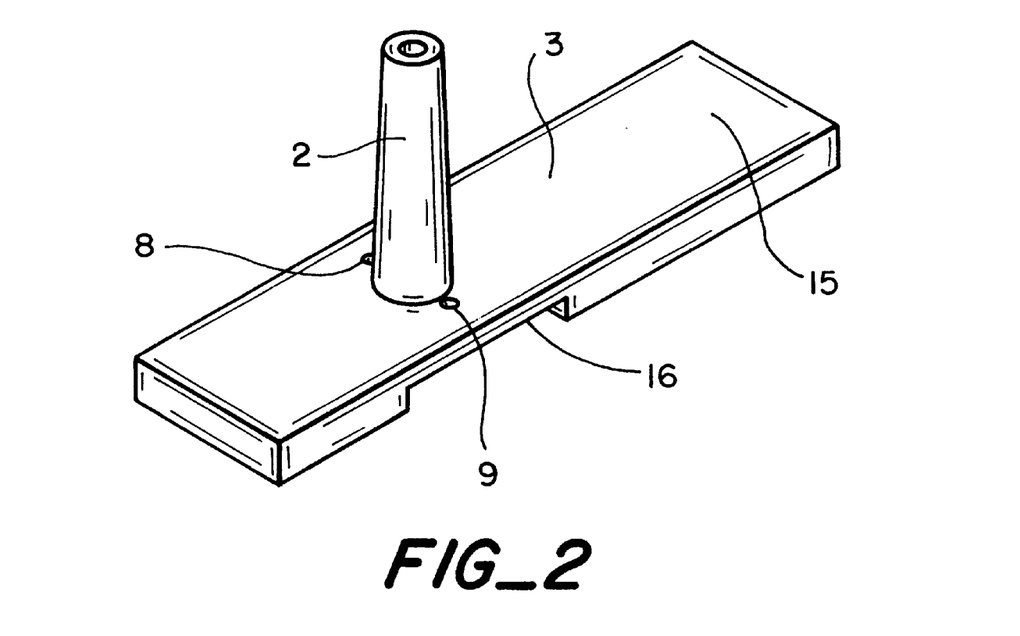
FIG. 2 is a perspective view of the injection molded capillary tube and support member including a handle.

FIG. 2 shows a detail perspective view of the injection molded capillary tube 2 and support member 3 which has capillary tube 2, handle area 15, vent holes 8 and 9, and slot 16 molded therein. The sample is wicked into the capillary tube 2. The materials which can be used to mold capillary tube 2 and support member 3 are selected for their wetability (hydrophilic) properties. These materials include polycarbonate, cellulosics and combinations of these with incorporated or added wetting agents such as polydimethylsiloxanes prepared as copolymers with alkene oxides. These materials are sold by United Chemical Technologies, Inc. Bristol, Pa. USA. The capillary tube inside diameter dimensions are selected such that adequate sample is drawn into the device and can range from less than 0.001 inches to 0.100 inches in diameter.

Figure 3:
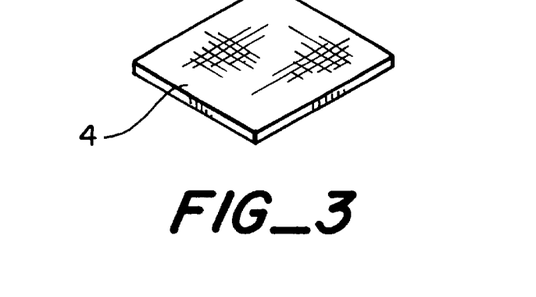
FIG. 3 is a perspective view of the spreading/filtering layer.

FIG. 3 shows the spreading layer/filter layer 4. This layer has high capillary action to draw the liquid sample into the device, transferring the sample to reagent layer membrane 5. The material of layer 4 is selected so that it can provide three beneficial purposes. The first is to provide capillary action to help draw the sample through the capillary tube 2. This provides the mechanism to empty the tube of the collected sample and disperse it onto the reagent layer membrane 5. A secondary function is to provide a filtering mechanism or pretreatment for the sample. Materials which have been proven to provide adequate capillary action are Ahlstrom 1281, 1660 and 1661. These materials are sold by Ahlstrom Filtration of Mt. Holly Springs, Pa. USA. The third benefit of the spreading layer 4 is it provides a light filter, i.e., when a dark material is used, it prevents light exposure onto the reagent layer membrane 5.

Figure 4:
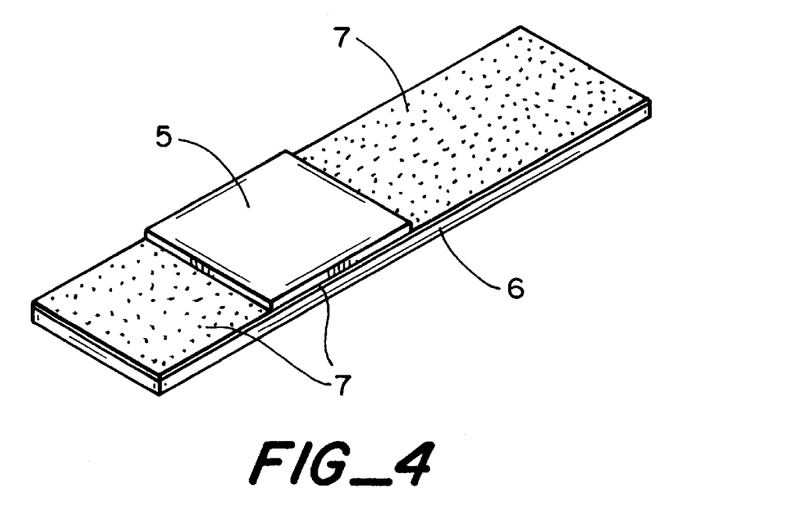
FIG. 4 is a perspective view of the reagent bearing membrane and carrier member.

FIG. 4 shows the reagent layer membrane 5 which is attached to the carrier layer 6 by adhesive layer 7. This subassembly is used to support the membrane reagent layer 5 during manufacture and provide protection for the fragile membrane 5. The membrane 5 has a reagent indicator system mixture applied to it to facilitate the indication of the presence or concentration of an analyte. The membrane which is preferred is Pall Gelman Sciences Supor 200, a polyethersulfone. The carrier layer 6 is preferably made from 0.005 inch thick polystyrene. However, any appropriate membrane or reagent layer material 5 can be used and the carrier layer or material 6 can be fashioned from a wide range of polymers or sheet material. The adhesive 7 is used to attach the membrane 5 to the carrier layer 6 and to attach the subassembly to support member 3. The adhesive 7 is first applied to the carrier layer 6. A test window 10 is cut into the strip to permit viewing the reaction if the carrier layer 6 is not a clear material or if the applied reagent system requires access to oxygen to adequately sense and indicate the analyte being tested.

Figure 5:
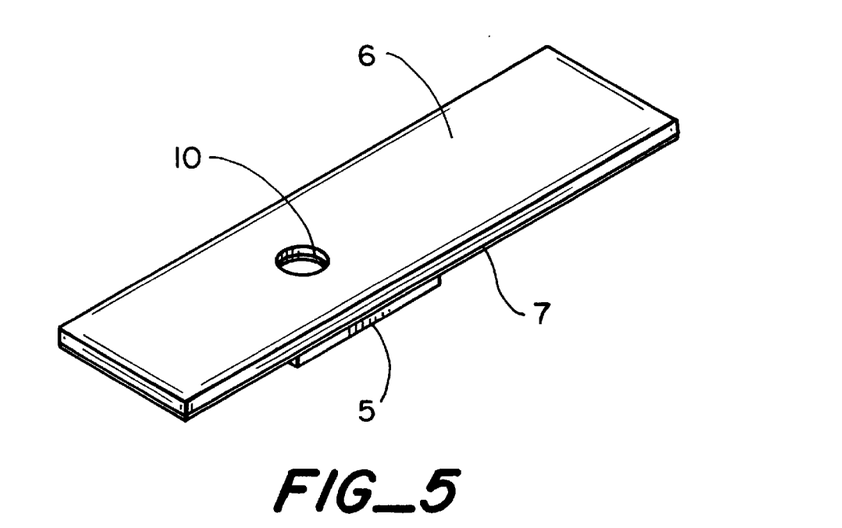
FIG. 5 is a perspective bottom view of the reagent bearing membrane and carrier member showing the aperture for reading the reagent indications.

FIG. 5 shows the carrier layer 6 and membrane 5 subassembly from the opposite side illustrating an embodiment with a test window or aperture 10.

Figure 6:
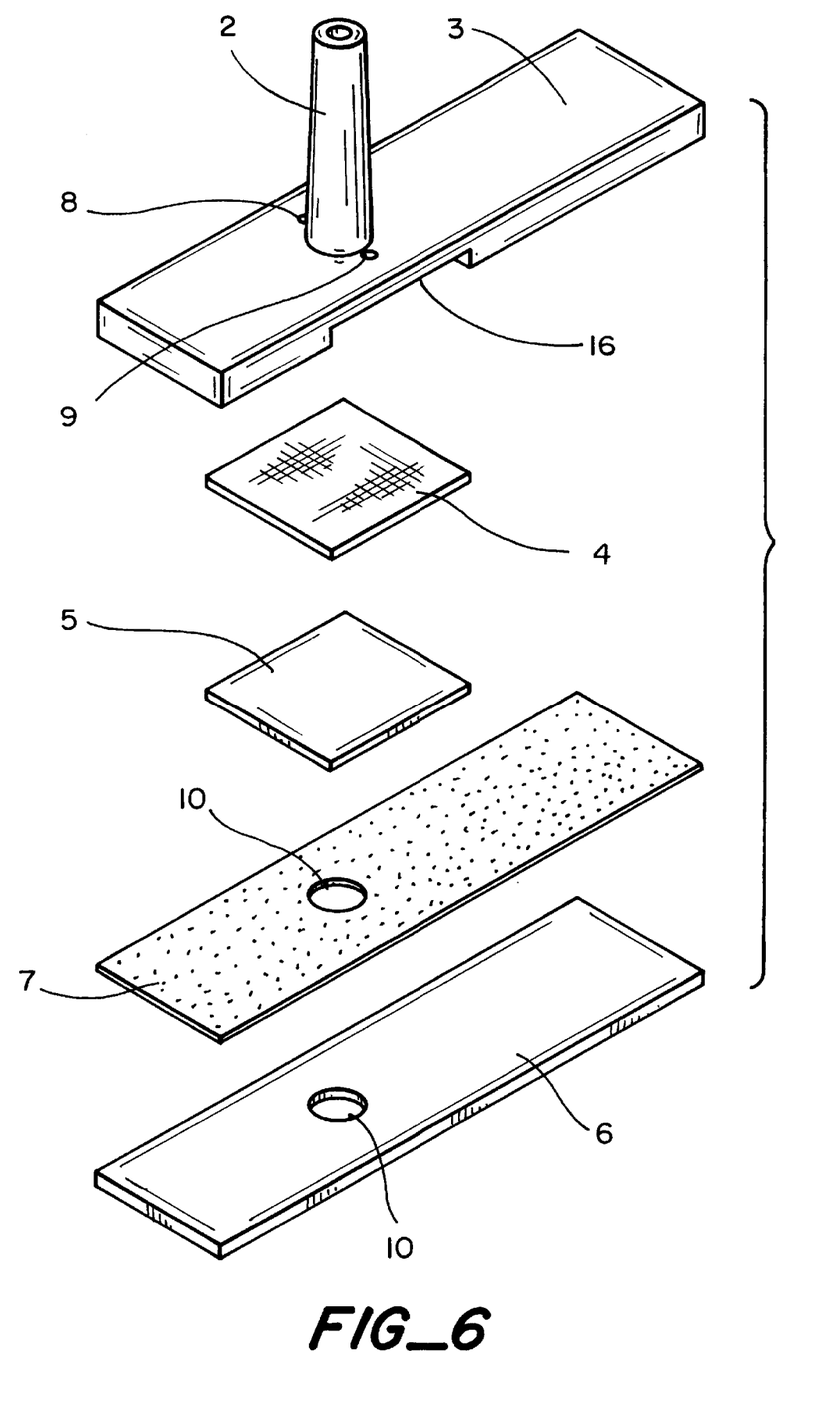
FIG. 6 is an exploded view of the capillary tube test strip assembly of FIG. 1.

FIG. 6 is an exploded view showing all the components in FIGS. 2 through 5 and how they are assembled to form the device of FIG. 1. The adhesive 7 is used to attach the carrier 6 and membrane 5 to the support member 3.

Figure 7:
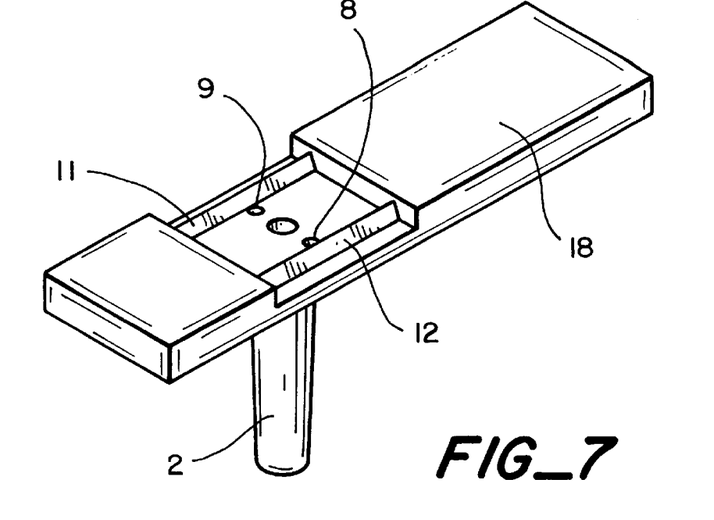
FIG. 7 is a perspective bottom view of an alternate capillary tube and support member, including handle, which provides barriers to define a specific volume for the microtitration.

FIG. 7 shows an alternate configuration of capillary tube 5 and support member 18. Support member 18 has dams or barriers 11 and 12 which are used to deform the spreading layer/filter 4 and membrane 5 forming a boundary for the absorption of the sample. The barriers create a predetermined volumetric space to provide the microtitration volume to enable accurate measurements. This deformation creates spreading layer/filter 17 shown in FIG. 8.

Figure 8:
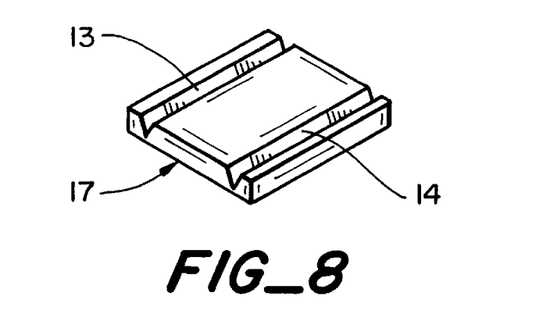
FIG. 8 is a perspective view of a compressed embossed spreading/filtering layer which fits into FIG. 7.

FIG. 8 shows spreading layer/filter 17 after it has been deformed into the shape conforming to the barrier members 11 and 12. This layer can include both spreading layer 4 laminated with reagent layer 5 to form element 17. Or the reagent layer 5 can be smaller in size so it fits between barrier members 11 and 12 so it is not deformed with spreading layer 4.

Figure 9:
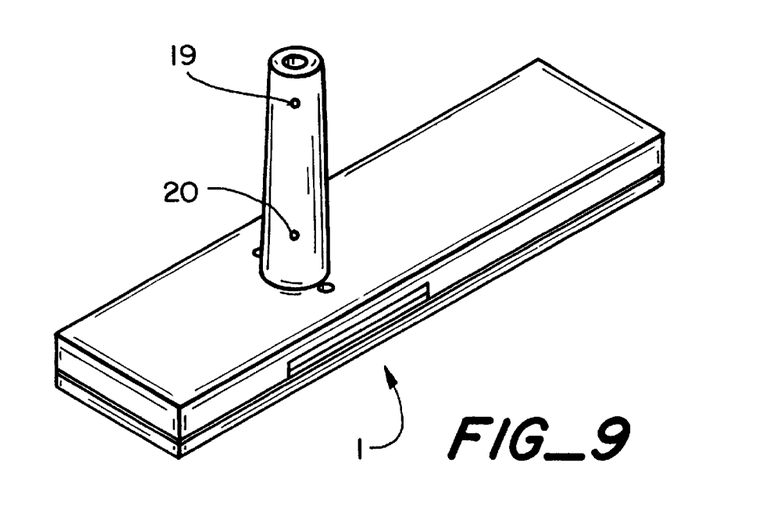
FIG. 9 is a perspective view of the capillary tube test strip assembly of this invention with sensors molded into the capillary tube for detection of the presence of and sequential flow of liquid through the tube.

FIG. 9 shows the capillary test strip with sensors 19 and 20 molded into the capillary tube for use as explained above.

In general the membrane material or reagent layer, 5 such as illustrated in FIG. 6, will generally be in the ranges of about 0.003" to 0.007" in thickness. In most test devices a thickness of about 0.004" to 0.005" is preferred. The carrier layer 6 in FIG. 6 will generally be a polymeric strip having a thickness from about 0.005" to about 0.012" in most applications and depending on the type of polymeric strip employed a thickness of about 0.007" to 0.008" is preferred. The carrier layer 6 is preferable a transparent layer so the reagent layer 5 can be read by a meter through carrier layer 6 without possibility of contamination of the meter. The injection molded capillary tube 2 and support member 3 in FIG. 2 can also have a thickness of from about 0.005" to about 0.020" with about 0.010" to 0.015" in thickness being preferred. The capillary tube 2 and support member 3 may also be made of a metal foil such as aluminum in which case the support member 3 may have a thickness of about 0.001" to 0.003" in thickness. Capillary tube 2 and support member 3 are preferably molded as a single unit, but can be molded or made separately, then pressed or attached together. The capillary tube can be placed at an angle ranging from 15 through 90 degrees relative to the surface of the support member. The tube 2 can be any desired shape, cylindrical, rectangular, square, elliptical, etc., so long as it functions with layers 4 and 5 (or 17) to wick the desired volume of sample fluid into the device. The tube will typically be 0.2" in length with an inside diameter to provide a 1 to 5 microlitre sample size.

It will be recognized by those skilled in the art that the overall thickness of the assembled test strip devices according to this invention may vary according to the desired use. The overall thickness of the assembled devices can range from about 0.006" to about 0.040". Due to the strength provided by laminating the various layers thinner layered materials may be used and provide sufficient strength. However, the overall thickness of a test strip device according to this invention will be determined also by the necessary and desired thickness of the matrix member to provide sufficient volume absorption. The shape need not be flat, but may be other shape desired for manufacturing efficiency, e.g., cylindrical, or for ease of handling by the user.

When the spreading layer/filter 17 and membrane 5 are compressed into the injection molded capillary tube and support member 18 as in FIGS. 7 and 8, the typical composite material having a thickness of about 0.005" to about 0.012" will be compressed at the barrier members 11 and 12 to a thickness of about 0.001" or less and typically less than about 0.0005". At the same time the portion of the matrix layer which protrudes into the volumetric opening will remain at or near its full original thickness.

The devices of this invention are conveniently made into test strips of convenient size and configuration for use by individuals and in instruments or meters which are adapted to measure the color or other indication provided by the test strips.

One example of a material useful for transfer of fluid containing analyte and blocking transfer of solids is a composite cellulose and glass fiber matrix, such as that available from Ahlstrom as part number 1661 or 1662, especially to separate the whole blood into red blood cells and substantially clear fluid. The whole blood is applied to the capillary and wicks into the matrix material. The use of a capillary tube to collect the sample permits the patient to collect a sample from a non finger tip location thereby increasing the number of possible sampling sites from which to extract a sample of body fluid. As the sample wicks, the red blood cells adhere to the glass fibers or other matrix fibers and the clear fluid moves vertically into the membrane test area where the dry reagents are present. The reagents in the membrane are rehydrated by the fluid component of the whole blood and are then able to indicate the presence and concentration of one or more analytes of interest. Separating agents impregnated into the matrix or membrane can assist with the separation of red blood cells and facilitate the wicking of the substantially clear fluid into the test area. This configuration coupled with microtitration and methods described above will produce an accurate test device.

The following is an example of making and using the devices of this invention.

EXAMPLES

Glucose Test

| Example A: | Test Reagents |
|---|---|
| Reagent 1a | 40 mg MBTH-S |
| | 80 mg DMAB |
| | 5 ml acetonitrile and 5 ml water |
| | Stir until all solids are dissolved. |
| Reagent 2a | 6 ml water |
| | 10 mg EDTA, disodium salt |
| | 200 mg PolyPep, low viscosity (Sigma) |
| | 0.668 g sodium citrate |
| | 0.523 g citric acid as a hematocrit adjuster |
| | 0.2 M Aconitic acid buffer |
| | 3% polyethylene glycol (PEG), as a separating agent |
| | 0.5% Polyquart, a binder |
| | 2.0 ml 6 wt % Gantrez AN-139 dissolved in wtaer (GAF) |
| | 30 mg horseradish peroxidase, 100 units/mg, and 3.0 glucose oxidase, 2000 units/ml |
| | Stir until dissolved. |

| Example B: | Test Reagents |
|---|---|
| Reagent 1b | 20 ml water |
| | 420 mg citric acid (a buffering agent). Adjust the pH of the citric acid solution with NaOH to a value of 4.25. |
| | 16.7 mg EDTA |
| | 90 mg Gantrez S95 available from GAF |
| | 250 mg Crotein SPA |
| | 20,500 units glucose oxidase |
| | 16,200 units peroxidase |
| Reagent 2b | 10 ml of a mixture of 3 parts by volume water and 7 parts by volume isopropyl alcohol |
| | 13 mg MBTH-S |
| | 40 mg ANS |

Polyethersulfone Matrix

A piece of polyethersulfone membrane is uniformly coated with reagent 1a; the excess is squeegied off and the material is dried. The membrane is then coated with reagent 2a in the same fashion and dried. The membrane is then assembled into a test device as shown in FIG. 1. Whole blood is applied to the capillary opening and the glucose level is read from the front based on the indicator response in the test zone.

We claim:

1. A strip for testing for the presence or concentration of an analyte in a fluid comprising:

a support member;

a spreading layer on a first side of the support member;

a reagent layer on the spreading layer which comprises a reagent selected for the analyte of interest; and a capillary tube attached to a side of the support member opposite from said first side communicating through an aperture in the support member with the spreading layer, whereby a fluid containing an analyte introduced into the tube flows through the tube and the spreading layer to contact the reagent.

2. A test strip according to claim 1 comprising a carrier layer on the reagent layer and positioned on a side of the reagent layer opposite from the spreading layer; and an aperture in the carrier layer for observing or measuring an indication of the reagent to determine the presence or concentration of the analyte.

3. A test strip according to claim 1 comprising a vent opening in the support member communicating with the spreading layer or the reagent layer for expulsion of air when fluid flows through the tube.

4. A test strip according to claim 2 comprising a vent opening in the carrier layer communicating with the spreading layer or the reagent layer for expulsion of air when fluid flows through the tube.

5. A test strip according to claim 1 comprising a sensor in the capillary tube for electrical detection of the presence of liquid at a preselected point in the tube.

6. A test strip according to claim 2 comprising barrier members defining a predetermined volume of the spreading layer and reagent layer in communication with the tube.

7. A test strip according to claim 1 wherein the capillary tube is positioned at an angle from about 15° through 90° relative to the surface of the support member.

8. A test strip according to claim 1 comprising a filtering layer positioned between the tube and the reagent layer for separating suspended solid materials from the liquid flowing from the tube to the reagent layer.

9. A test strip according to claim 1 wherein the support member contains a recessed area for receiving the spreading layer and reagent layer.

10. A test strip according to claim 2 wherein the support member contains a recessed area for receiving the spreading layer and reagent layer.

11. A method of testing a fluid for the presence or concentration of an analyte comprising:

providing a test strip comprising:

a support member;

a spreading layer on a first side of the support member;

a reagent layer on the spreading layer which comprises a reagent selected for the analyte of interest; and a capillary tube attached to a side of the support member opposite said first side communicating through an aperture in the support member with the spreading layer, whereby a fluid containing an analyte introduced into the tube flows through the tube and the spreading layer to contact the reagent;

introducing sufficient fluid containing the analyte into the capillary tube to flow onto the reagent layer; and observing or measuring an indication of the reagent to determine the presence or concentration of the analyte.

12. A method according to claim 9 comprising measuring the indication of the reagent with an electronic meter.

* * * * *